United States Patent [19]

Rajadhyaksha

[11] 4,405,616

[45] Sep. 20, 1983

[54] PENETRATION ENHANCERS FOR TRANSDERMAL DRUG DELIVERY OF SYSTEMIC AGENTS

[75] Inventor: Vithal J. Rajadhyaksha, Mission Viejo, Calif.

[73] Assignee: Nelson Research & Development Company, Irvine, Calif.

[21] Appl. No.: 380,161

[22] Filed: May 20, 1982

Related U.S. Application Data

[63] Continuation-in-part of Ser. No. 260,201, May 4, 1981, abandoned, which is a continuation of Ser. No. 725,490, Oct. 28, 1976, abandoned, which is a continuation-in-part of Ser. No. 588,247, Jul. 19, 1975, Pat. No. 3,989,816.

[51] Int. Cl.³ ............................................. A61K 31/33
[52] U.S. Cl. .................................................. 424/244
[58] Field of Search ......................................... 424/244

*Primary Examiner*—Stanley J. Friedman
*Attorney, Agent, or Firm*—Martin A. Voet

[57] ABSTRACT

In a method for administering systemically active agents including therapeutic agents through the skin or other body membranes of humans and animals typically in the form of a transdermal device or formulation, the improvement comprising the use therewith of an effective amount of a membrane penetration enhancer having the structural formula.

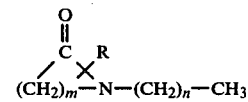

wherein R is H or a lower alkyl group, m is 5-7 and n is 0-17.

7 Claims, No Drawings

PENETRATION ENHANCERS FOR TRANSDERMAL DRUG DELIVERY OF SYSTEMIC AGENTS

REFERENCE TO EARLIER FILED APPLICATIONS

This application is a continuation-in-part of U.S. Ser. No. 260,201 filed May 4, 1981, now abandoned, which in turn is a continuation of Ser. No. 725,490, filed Oct. 28, 1976, now abandoned, which was a continuation-in-part of Ser. No. 588,247, filed July 19, 1975, now U.S. Pat. No. 3,989,816.

BACKGROUND OF THE INVENTION

1. Field of the Invention

The invention generally relates to an improved method of drug delivery. More particularly, the invention relates to an improved membrane penetration enhancer for use in the transdermal delivery of systemically active drugs to humans and animals.

2. Background of the Prior Art

For some years, pharmaceutical researchers have sought an effective means of introducing drugs into the bloodstream by applying them to unbroken skin. Among other advantages, such administration can provide a comfortable, convenient, and safe way of giving many drugs now taken orally or infused into veins or injected intramuscularly.

Using skin as the portal for drug entry offers unique potential, because transdermal delivery permits close control over drug absorption. For example, it avoids factors that can cause unpredictable absorption from the gastrointestinal tract, including: changes in acidity, motility, and food content. It also avoids initial metabolism of the drug by the liver. Thus, controlled drug entry through skin can achieve a high degree of control over blood concentrations of drug.

Close control over drug concentrations in blood can translate readily into safer and more comfortable treatment. When a drug's adverse effects occur at higher concentrations than its beneficial ones, rate control can maintain the concentrations that evoke only—or principally the drug's desired actions. This ability to lessen undesired drug actions can greatly reduce the toxicity hazards that now restrict or prevent the use of many valuable agents.

Transdermal delivery particularly benefits patients with chronic disease. Many such patients have difficulty following regimens requiring several doses daily of medications that repeatedly cause unpleasant symptoms. They find the same drugs much more acceptable when administered in transdermal systems that require application infrequently—in some cases, only once or twice weekly—and that reduce adverse effects.

Transdermal delivery is feasible for drugs effective in amounts that can pass through the skin area and that are substantially free of localized irritating or allergic effects. While these limitations may exclude some agents, many others remain eligible for transdermal delivery. Moreover, their numbers will expand as pharmaceutical agents of greater potency are developed. Particularly suitable for transdermal delivery are potent drugs with only a narrow spread between their toxic and safe blood concentrations, those having gastrointestinal absorption problems, or those requiring frequent dosing in oral or injectable form.

Transdermal therapy permits much wider use of natural substances such as hormones. Often the survival times of these substances in the body are so short that they would have to be taken many times daily in ordinary dosage forms. Continuous transdermal delivery provides a practical way of giving them, and one that can mimic the body's own patterns of secretion.

At present, controlled transdermal therapy appears feasible for many drugs used for a wide variety of ailments including, but not limited to, circulatory problems, hormone deficiency, respiratory ailments, and pain relief.

Percutaneous administration can have the advantage of permitting continuous administration of drug to the circulation over a prolonged period of time to obtain a uniform delivery rate and blood level of drug. Commencement and termination of drug therapy are initiated by the application and removal of the dosing devices from the skin. Uncertainties of administration through the gastrointestinal tract and the inconvenience of administration by injection are eliminated. Since a high concentration of drug never enters the body, problems of pulse entry are overcome and metabolic half-life is not a factor of controlling importance.

My related U.S. Pat. No. 3,989,816 generally describes a method for enhancing the topical (as contrasted by the systemic) administration of physiologically active agents by combining such an agent with an effective amount of a penetration enhancer of the type disclosed herein and applying the combination topically to humans or animals, in the form of creams, lotions, gels, etc.

Penetration enhancers for enhancing systemic administration of theraputic agents transdermally disclosed in the art include dodecyl pyrrolidone, dimethyl lauramide and dimethyl sulfoxide. The prior art states that these agents may be used prior to or concurrently with administration of the active agent, e.g. see U.S. Pat. Nos. 4,031,894, 3,996,934 and 3,921,636.

SUMMARY OF THE INVENTION

I have now discovered that the penetration enhancers previously disclosed in U.S. Pat. No. 3,989,816 to enhance topical delivery of physiologically active agents also enhance the transdermal delivery of systemically active agents through the skin or other body membranes of humans and animals directly into the bloodstream.

The invention therefore relates to an improved method for administering systemically active agents through the skin or other body membranes of humans and animals, utilizing a transdermal device or formulation, the improvement comprising the use therewith of an effective amount of a membrane penetration enhancer having the structural formula

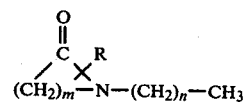

where R is H or a lower alkyl group having 1–4 carbon atoms, m is 5–7 and n is 0–17.

The invention also relates to an improved method for administering systemically active theraputic agents topically through the skin of humans in a transdermal device or formulation to obtain therapeutic levels of the therapeutic agent, the improvement comprising the use therewith of an effective skin penetration enhancing amount of 1-dodecylazacycloheptan-2-one.

In one preferred embodiment, R is H, m is 5 and n is 0–17. In another preferred embodiment, R is H, m is 7 and n is 0–17. The preferred compound is 1-n-dodecylazacycloheptan-2-one.

DETAILED DESCRIPTION OF THE INVENTION

The described 1-substituted azacycloalkan-2-ones are made by methods disclosed in U.S. Pat. No. 4,316,893, the applicable portions of which are hereby incorporated by this reference.

Typical systemically active agents which may be delivered transdermally are therapeutic agents which are sufficiently potent such that they can be delivered through the skin or other membrane to the bloodstream in sufficient quantities to produce the desired therapeutic effect. In general, this includes therapeutic agents in all of the major therapeutic areas including, but not limited to, anti-infectives, such as antibiotics and antiviral agents, analgesics and analgesic combinations, anorexics, anthelmintics, antiarthritics, antiasthma agents, anticonvulsants, antidepressants, antidiabetic agents, antidiarrheals, antihistamines, anti-inflammatory agents, antimigraine preparations, antimotion sickness, antinauseants, antineoplastics, antiparkinsonism drugs, antipruritics, antipsychotics, antipyretics, antispasmodics, including gastrointestinal and urinary; anticholinergics, sympathomimetics, xanthine derrivatives, cardiovascular preparations including calcium channel blockers, beta-blockers, antiarrhythmics, antihypertensives, diuretics, vasodilators including general, coronary, peripheral and cerebral; central nervous system stimulants, cough and cold preparations, decongestants, diagnostics, hormones, hypnotics, immunosuppressives, muscle relaxants, parasympatholytics, parasympathomimetics, psychostimulants, sedatives and tranquilizers.

Dosage forms for application to the skin or other membranes of humans and animals incude creams, lotions, gels, ointments, suppositories, sprays, aerosols, buccal and sub-lingual tablets and any one of a varietary of transdermal devices for use in the continuous administration of systemically active drugs by absorption through the skin, oral mucosa or other membranes, see, for example, one or more of U.S. Pat. Nos. 3,598,122, 3,598,123, 3,731,683, 3,742,951, 3,814,097, 3,921,636, 3,972,995, 3,993,072, 3,993,073, 3,996,934, 4,031,894, 4,060,084, 4,069,307, 4,201,211, 4,230,105, 4,292,299 and 4,292,303. U.S. Pat. No. 4,077,407 and the foregoing patents also disclose a variety of specific systemically active agents which may also be useful in transdermal delivery, which disclosures are hereby incorporated herein by this reference.

Typical inert carriers which may be included in the foregoing dosage forms include conventional formulating materials, such as, for example, water, isopropyl alcohol, freons, ethyl alcohol, polyvinyl pyrrolidone, propylene glycol, fragrances, gel-producing materials such as "Carbopol", stearyl alcohol, stearic acid, spermaceti, sorbitan monooleate, "Polysorbates", "Tweens", sorbital, methylcellulose, etc.

Systemically active agents are used in amounts calculated to achieve and maintain therapeutic blood levels in a human or animal over the period of time desired. These amounts vary with the potency of each systemically active substance, the amount required for the desired therapeutic or other effect, the rate of elimination or breakdown of the substance by the body once it has entered the bloodstream and the amount of penetration enhancer in the formulation. In accordance with conventional prudent formulating practices, a dosage near the lower end of the useful range of a particular agent is usually employed initially and the dosage increased or decreased as indicated from the observed response, as in the routine procedure of the physician.

The amount of penetration enhancer which may be used in the invention varies from about 1 to 100 percent although adequate enhancement of penetration is generally found to occur in the range of about 1 to about 10 percent by weight of the formulation to be delivered. The penetration enhancer disclosed herein may be used in combination with the active agent or may be used separately as a pre-treatment of the skin or other body membrane through which the active agent is intended to be delivered.

I claim:

1. In a method for topically administering systemically active agents through the skin or mucosal membranes of humans and animals in a transdermal device or formulation, the improvement comprising the topical administration of an effective amount of a membrane penetration enhancer having the structural formula

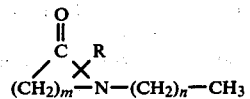

where R is H or a lower alkyl group having 1–4 carbon atoms, m is 5 and n is 0–17.

2. The method of claim 1 wherein R is H.

3. The method of claim 2 wherein n is 0–11.

4. The method of claim 1 wherein the penetration enhancer is 1-dodecylazacycloheptan-2-one.

5. The method of claim 1 wherein the systemically active agent is a therapeutic agent.

6. The method of claim 5 wherein the administration is concurrent.

7. In a method for topically administering a systemically active therapeutic agent through the skin of a human in a transdermal device or formulation to obtain therapeutic blood levels of the therapeutic agent, the improvement comprising the concurrent topical administration of an effective skin penetration enhancing amount of 1-dodecylazacycloheptan-2-one.

* * * * *